(12) United States Patent
Shibata

(10) Patent No.: US 11,080,473 B2
(45) Date of Patent: Aug. 3, 2021

(54) INFORMATION PROCESSING DEVICE, METHOD FOR CONTROLLING INFORMATION PROCESSING DEVICE, PROGRAM, AND WEB SERVER

(71) Applicant: Rakuten, Inc., Tokyo (JP)

(72) Inventor: Mitsuru Shibata, Tokyo (JP)

(73) Assignee: Rakuten, Inc., Tokyo (JP)

( * ) Notice: Subject to any disclaimer, the term of this patent is extended or adjusted under 35 U.S.C. 154(b) by 250 days.

(21) Appl. No.: 14/428,675

(22) PCT Filed: Sep. 24, 2012

(86) PCT No.: PCT/JP2012/074410
§ 371 (c)(1),
(2) Date: Mar. 17, 2015

(87) PCT Pub. No.: WO2014/045443
PCT Pub. Date: Mar. 27, 2014

(65) Prior Publication Data
US 2015/0242954 A1 Aug. 27, 2015

(51) Int. Cl.
*G06F 40/174* (2020.01)
*G16H 40/67* (2018.01)
(Continued)

(52) U.S. Cl.
CPC .......... *G06F 40/174* (2020.01); *G06F 3/0482* (2013.01); *G06F 3/04842* (2013.01); *G06Q 40/08* (2013.01); *G16H 40/67* (2018.01)

(58) Field of Classification Search
CPC ...... G06Q 40/08; G06Q 50/22; G06F 3/0482; G06F 3/04842; G06F 17/243
(Continued)

(56) References Cited

U.S. PATENT DOCUMENTS 5,845,300 A * 12/1998 Comer .................... G06F 40/18
715/203
6,651,217 B1 * 11/2003 Kennedy ............... G06F 40/174
715/224
(Continued)

FOREIGN PATENT DOCUMENTS

JP 2001-167160 A 6/2001
JP 2003-44781 A 2/2003
(Continued)

OTHER PUBLICATIONS

"Surveys with Skip Logic and Conditional Branching"; objectplanet; <http://www.objectplanet.com/opinio/surveys-with-skip-logic.html>; published prior to Nov. 5, 2009.*
(Continued)

*Primary Examiner* — Stephen S Hong
*Assistant Examiner* — Broderick C Anderson
(74) *Attorney, Agent, or Firm* — Sughrue Mion, PLLC

(57) ABSTRACT

Display control means (52) of an information processing device (1) displays, on a screen, respective input forms of plurality of disclosure items relating to a health condition of a policyholder. Receiving means (58) receives input of the disclosure statement in each of the input forms by the user. First input control means (62) inputs the disclosure statement into the input form in which the user has input the disclosure statement. In a case where the user inputs the disclosure statement into one of the input forms of the plurality of disclosure items, second input control means (66) inputs, into the input form, the disclosure statement that is input into the input form of another disclosure item associated with the disclosure item.

25 Claims, 12 Drawing Sheets

(51) Int. Cl.
*G06Q 40/08* (2012.01)
*G06F 3/0482* (2013.01)
*G06F 3/0484* (2013.01)

(58) Field of Classification Search
USPC .......................................................... 715/224
See application file for complete search history.

(56) References Cited

U.S. PATENT DOCUMENTS

| | | | | |
|---|---|---|---|---|
| 7,426,496 | B2* | 9/2008 | Kristjansson | G06F 40/174 |
| | | | | 706/10 |
| 7,685,144 | B1* | 3/2010 | Katragadda | G06F 3/0237 |
| | | | | 707/999.101 |
| 7,908,287 | B1* | 3/2011 | Katragadda | G06F 3/0237 |
| | | | | 707/723 |
| 2002/0026103 | A1* | 2/2002 | Norris | A61B 5/0031 |
| | | | | 600/300 |
| 2002/0138462 | A1* | 9/2002 | Ricketts | G06F 40/174 |
| 2005/0257134 | A1* | 11/2005 | Goodman | G06F 17/243 |
| | | | | 715/226 |
| 2009/0204881 | A1* | 8/2009 | Murthy | G06F 17/243 |
| | | | | 715/226 |
| 2015/0286802 | A1* | 10/2015 | Kansara | G16H 10/20 |
| | | | | 705/3 |

FOREIGN PATENT DOCUMENTS

| | | |
|---|---|---|
| JP | 2003-67577 A | 3/2003 |
| JP | 2004-102340 A | 4/2004 |
| JP | 2008-299744 A | 12/2008 |
| JP | 2011-233143 A | 11/2011 |
| JP | 2012-93810 A | 5/2012 |

OTHER PUBLICATIONS

Jotform, "How to Give Users the Ability to Easily Copy Content from One Field to Another"; <Users the Ability to Easily Copy Content from One Field to Another>; published Nov. 4, 2011 (Year: 2011).*

Akiko Kitami, "Mendo na Data Nyuryoku o Koritsuteki ni! 'Nyuryoku Shien', 'Control' o Full Katsuyo", Nikkei PC21, Mar. 24, 2012, p. 101, vol. 17, No. 7.

International Search Report for PCT/JP2012/074410 dated Dec. 18, 2012.

* cited by examiner

FIG.2

DISCLOSURE: HEALTH CONDITION

CURRENT HEALTH CONDITION

| 1 | HAVE YOU RECEIVED CONSULTATION/ EXAMINATION/TREATMENT/MEDICATION/ BY A DOCTOR IN THE LAST THREE MONTHS? | ○ NO | ○ YES |
|---|---|---|---|

HEALTH CONDITION IN LAST FIVE YEARS

| 2 | HAVE YOU BEEN HOSPITALIZED FOR A CONTINUOUS PERIOD OF SEVEN DAYS OR MORE FOR INJURY OR DISEASE IN THE LAST FIVE YEARS? | ○ NO | ○ YES |
|---|---|---|---|

| 3 | HAVE YOU HAD SURGERY FOR INJURY OR DISEASE IN THE LAST FIVE YEARS? | ○ NO | ○ YES |
|---|---|---|---|

HEALTH CONDITION IN LAST TWO YEARS

| 4 | HAVE YOU HAD MEDICAL CHECKUP/CANCER SCREENING/THOROUGH PHYSICAL EXAMINATION IN THE LAST TWO YEARS? | ○ NO | ○ YES |
|---|---|---|---|

| 5 | IF "YES" IN 4, WAS ANY ABNORMALITY FOUND? | ○ NO | ○ YES |
|---|---|---|---|

PHYSICAL DISABILITY

| 6 | DO YOU HAVE HANDICAP OF VISION/HEARING /SPEAKING/MASTICATORY IMPAIRMENT? | ○ NO | ○ YES |
|---|---|---|---|

| 7 | DO YOU HAVE FUNCTIONAL DISORDER OR AMPUTATION IN HAND/ARM/FOOT/LEG/ FINGER? | ○ NO | ○ YES |
|---|---|---|---|

PREEXISTING CONDITIONS OF CANCER

| 8 | HAVE YOU OR ARE YOU SUFFERED FROM CANCER? | ○ NO | ○ YES |
|---|---|---|---|

DISCLOSURE: HEALTH CONDITION

CURRENT HEALTH CONDITION

| 1 | HAVE YOU RECEIVED CONSULTATION/ EXAMINATION/TREATMENT/MEDICATION/ BY A DOCTOR IN THE LAST THREE MONTHS? | ○ NO  ◉ YES |

31A / 32A

▼ PLEASE GO ON TO ENTER THE DETAILS.

| INJURY/DISEASE NAME/ EXAMINATION NAME | | ← 33A |
|---|---|---|
| PERIOD OF TREATMENT /EXAMINATION AND CURRENT CONDITION | ▼ FROM YEAR  ▼ MONTH  ▼ TO YEAR  ▼ MONTH | ← 34A |
| | CURRENTLY: ○ FULLY-HEALED  ○ UNDER TREATMENT  ○ FOLLOW-UP | ← 35A |
| TREATMENT/ EXAMINATION | ☐ EXAMINATION/CONSULTATION/INTERVIEW  ☐ MEDICATION  ☐ HOSPITAL VISIT  ☐ HOSPITALIZATION  ☐ SURGERY | ← 36A |
| MEDICAL INSTITUTION | | ← 37A |
| DETAILS | | ← 38A |

HEALTH CONDITION IN LAST FIVE YEARS

| 2 | HAVE YOU BEEN HOSPITALIZED FOR A CONTINUOUS PERIOD OF SEVEN DAYS OR MORE FOR INJURY OR DISEASE IN THE LAST FIVE YEARS? | ○ NO  ○ YES |

31B / 32B

| 3 | HAVE YOU HAD SURGERY FOR INJURY OR DISEASE IN THE LAST FIVE YEARS? | ○ NO  ○ YES |

DISCLOSURE: HEALTH CONDITION

CURRENT HEALTH CONDITION

| 1 | HAVE YOU RECEIVED CONSULTATION/ EXAMINATION/TREATMENT/MEDICATION/ BY A DOCTOR IN THE LAST THREE MONTHS? | ○ NO  ● YES |
|---|---|---|

▼ PLEASE GO ON TO ENTER THE DETAILS.

| INJURY/DISEASE NAME/ EXAMINATION NAME | STOMACH CANCER |
|---|---|
| PERIOD OF TREATMENT /EXAMINATION AND CURRENT CONDITION | [2010▼] FROM YEAR [4▼] MONTH [2010▼] TO YEAR [7▼] MONTH |
| | CURRENTLY: ● FULLY-HEALED ○ UNDER TREATMENT ○ FOLLOW-UP |
| TREATMENT/ EXAMINATION | ☐ EXAMINATION/CONSULTATION/INTERVIEW ☐ MEDICATION ☐ HOSPITAL VISIT ☑ HOSPITALIZATION ☑ SURGERY |
| MEDICAL INSTITUTION | AAA CLINIC |
| DETAILS | RECOVERED FROM EARLY-STAGE STOMACH CANCER BY SURGERY······ ······ |

HEALTH CONDITION IN LAST FIVE YEARS

| 2 | HAVE YOU BEEN HOSPITALIZED FOR A CONTINUOUS PERIOD OF SEVEN DAYS OR MORE FOR INJURY OR DISEASE IN THE LAST FIVE YEARS? | ○ NO  ● YES |
|---|---|---|

▼ PLEASE GO ON TO ENTER THE DETAILS.

| INJURY/DISEASE NAME/ EXAMINATION NAME | |
|---|---|
| PERIOD OF TREATMENT /EXAMINATION AND CURRENT CONDITION | [▼] FROM YEAR [▼] MONTH [▼] TO YEAR [▼] MONTH |
| | CURRENTLY: ○ FULLY-HEALED ○ UNDER TREATMENT ○ FOLLOW-UP |
| TREATMENT/ EXAMINATION | ☐ EXAMINATION/CONSULTATION/INTERVIEW ☐ MEDICATION ☐ HOSPITAL VISIT ☐ HOSPITALIZATION ☐ SURGERY |
| MEDICAL INSTITUTION | |
| DETAILS | |

FIG.5

DISCLOSURE: HEALTH CONDITION

CURRENT HEALTH CONDITION

| 1 | HAVE YOU RECEIVED CONSULTATION/ EXAMINATION/TREATMENT/MEDICATION/ BY A DOCTOR IN THE LAST THREE MONTHS? | ○ NO  ● YES |
|---|---|---|

▼ PLEASE GO ON TO ENTER THE DETAILS.

| INJURY/DISEASE NAME/ EXAMINATION NAME | STOMACH CANCER |
|---|---|
| PERIOD OF TREATMENT /EXAMINATION AND CURRENT CONDITION | 2010 ▼ FROM YEAR  4 ▼ MONTH  2010 ▼ TO YEAR  7 ▼ MONTH |
| | CURRENTLY: ● FULLY-HEALED  ○ UNDER TREATMENT  ○ FOLLOW-UP |
| TREATMENT/ EXAMINATION | ☐ EXAMINATION/CONSULTATION/INTERVIEW  ☐ MEDICATION  ☐ HOSPITAL VISIT  ☑ HOSPITALIZATION  ☑ SURGERY |
| MEDICAL INSTITUTION | AAA CLINIC |
| DETAILS | RECOVERED FROM EARLY-STAGE STOMACH CANCER BY SURGERY······ ······ |

HEALTH CONDITION IN LAST FIVE YEARS

| 2 | HAVE YOU BEEN HOSPITALIZED FOR A CONTINUOUS PERIOD OF SEVEN DAYS OR MORE FOR INJURY OR DISEASE IN THE LAST FIVE YEARS? | ○ NO  ● YES |
|---|---|---|

▼ PLEASE GO ON TO ENTER THE DETAILS.

| INJURY/DISEASE NAME/ EXAMINATION NAME | |
|---|---|
| PERIOD OF TREATMENT /EXAMINATION AND CURRENT CONDITION | STOMACH CANCER  C  ▼月まで |
| | CURRENTLY: ○ FULLY-HEALED  ○ UNDER TREATMENT  ○ FOLLOW-UP |
| TREATMENT/ EXAMINATION | ☐ EXAMINATION/CONSULTATION/INTERVIEW  ☐ MEDICATION  ☐ HOSPITAL VISIT  ☐ HOSPITALIZATION  ☐ SURGERY |
| MEDICAL INSTITUTION | |
| DETAILS | |

| GROUP | DISCLOSURE ITEM |
|---|---|
| Disease | NAME INPUT FORM 33A、33B、・・・・ |
| Hospital | MEDICAL INSTITUTION INPUT FORM 37A、37B、・・・・ |
| Comment ⋮ | TREATMENT/EXAMINATION DETAIL INPUT FORM 38A、38B、・・・・ ⋮ |

FIG.12

| DISCLOSURE ITEM | CONDITION |
|---|---|
| NAME INPUT FORM 33B | "HOSPITALIZATION" IS CHECKED IN CONDITION INPUT FORM 35 OF ANOTHER DISCLOSURE ITEM |
| NAME INPUT FORM 33H | "CANCER" IS INCLUDED IN NAME INPUT FORM 33 OF ANOTHER DISCLOSURE ITEM |
| ⋮ | ⋮ |

INFORMATION PROCESSING DEVICE, METHOD FOR CONTROLLING INFORMATION PROCESSING DEVICE, PROGRAM, AND WEB SERVER

CROSS REFERENCE TO RELATED APPLICATIONS

This application is a National Stage of International Application No. PCT/JP2012/074410 filed Sep. 24, 2012, the contents of which are incorporated herein by reference in their entirety.

TECHNICAL FIELD

The present invention relates to an information processing device, a method for controlling the information processing device, a program, and a web server.

BACKGROUND ART

There has been known an information processing device for receiving inputs of disclosure statements regarding health condition from a policyholder of life insurance or a medical insurance. For example, Patent Literature 1 describes customizing matters to disclose that a user needs to input based on a type of insurance applied by the user.

CITATION LIST

Patent Document

Patent Literature 1: JP2003-67577A

SUMMARY OF INVENTION

Technical Problem

A user needs to input various matters to disclose according to disclosure requirements when applying insurance, although conventional technique requires the user to repeatedly input the same content and imposes a burden on the user.

One or more embodiments of the present invention have been conceived in view of the above, and an object thereof is to provide an information processing device, a method for controlling the information processing device, a program, and a web server capable of reducing a user's burden required for inputting answers to disclosure requirements of insurance.

Solution to Problem

In order to solve the above described problems, an information processing device according to the present invention for receiving input of a disclosure statement relating to a health condition of a policyholder includes display control means for displaying a plurality of input forms for respective disclosure items on a screen, receiving means for receiving input of the disclosure statement in each of the input forms by a user, first input control means for inputting the disclosure statement into the input form, into which the user has input the disclosure statement, and second input control means for inputting, in a case where the user inputs the disclosure statement into one of the input forms of the plurality of disclosure items, the disclosure statement that has been input into the input form of another disclosure item associated with the disclosure item, into the input form.

A method for controlling an information processing device that receives input of a disclosure statement relating to a health condition of a policyholder according to the present invention, the method includes the steps of displaying a plurality of input forms for respective disclosure items on a screen, receiving input of the disclosure statement in each of the input forms by a user, inputting the disclosure statement into the input form, into which the user has input the disclosure statement, and inputting, in a case where the user inputs the disclosure statement into one of the input forms of the plurality of disclosure items, the disclosure statement that has been input into the input form of another disclosure item associated with the disclosure item, into the input form.

A program according to the present invention causes a computer, which receives input of a disclosure statement relating to a health condition of a policyholder, to function as display control means for displaying a plurality of input forms for respective disclosure items on a screen, receiving means for receiving input of the disclosure statement in each of the input forms by a user, first input control means for inputting the disclosure statement into the input form, into which the user has input the disclosure statement, and second input control means for inputting, in a case where the user inputs the disclosure statement into one of the input forms of the plurality of disclosure items, the disclosure statement that has been input into the input form of another disclosure item associated with the disclosure item, into the input form.

A web server according to the present invention includes means for sending the program to the computer.

In one embodiment of the present invention, the information processing device further includes means for displaying, in a case where the user inputs the disclosure statement into one of the input forms of the plurality of disclosure items, one or more disclosure statements that have been input into the input forms of one or more other disclosure items associated with the disclosure item, on the screen, and means for receiving the disclosure statement selected by the user among from the displayed disclosure statements. The second input control means inputs, into the input form, the disclosure statement selected by the user among from the displayed disclosure statements.

In one embodiment of the present invention, the information processing device further includes determining means for determining, in a case where the user inputs the disclosure statement into one of the input forms of the plurality of disclosure items, whether or not the disclosure statement that has been input into the input form of another disclosure item associated with the disclosure item to be input relates to the disclosure item to be input, and means for deciding whether or not to execute processing by the second input control means based on a determination result of the determining means.

In one embodiment of the present invention, the receiving means receives input from the user regarding a treatment or an examination of an injury/disease of the policyholder, and the determining means determines whether or not the treatment or the examination of the injury/disease that has been input into the input form of another disclosure item associated with the disclosure item to be input relates to the disclosure item to be input.

In one embodiment of the present invention, the receiving means receives input from the user regarding a name of an injury/disease or an examination of the policyholder, and the determining means determines whether or not the name of the injury/disease or the examination that has been input into the input form of another disclosure item associated with the disclosure item to be input is the name relating to the disclosure item to be input.

In one embodiment of the present invention, the receiving means receives input from the user regarding a period of a treatment or an examination of an injury/disease of the policyholder, and the determining means determines whether or not a period of the treatment or the examination of the injury/disease that has been input into the input form of another disclosure item associated with the disclosure item to be input is the period relating to the disclosure item to be input.

In one embodiment of the present invention, the information processing device further includes candidate display control means for displaying, in a case where the user inputs the disclosure statement into one of the input forms of the plurality of disclosure items, a plurality of disclosure statement candidates on the screen. The receiving means receives the input of the disclosure statement from the user by receiving the disclosure statement selected by the user from the plurality of disclosure statement candidates, and the candidate display control means preferentially displays the disclosure statement candidate that has been input into the input form of another disclosure item associated with the disclosure item to be input over other disclosure statement candidates.

In one embodiment of the present invention, the information processing device further includes means for restricting input of the disclosure statements into respective input forms by the user, means for releasing, in a case where a releasing operation associated with each of the plurality of disclosure items is performed, a restriction of the input into the input form of the disclosure item, means for determining, in a case where the user inputs the disclosure statement into the input form that is released from the restriction, whether or not the disclosure statement input by the user relates to another disclosure item, and means for assuming that the releasing operation of the another disclosure item is performed based on the determination result of the means.

Advantageous Effects of Invention

According to the present invention, it is possible to reduce a user's burden required for inputting disclosure statements of insurance.

BRIEF DESCRIPTION OF DRAWINGS

[FIG. 2] A diagram illustrating an example of a disclosure statement input screen to which a user inputs disclosure statements.

[FIG. 3] A diagram illustrating an example of the disclosure statement input screen when a radio button indicating "Yes" is selected.

[FIG. 4] A diagram illustrating an example of the disclosure statement input screen when a radio button indicating "Yes" is selected.

[FIG. 5] A diagram illustrating an example of the disclosure statement input screen when a name input form is focused.

[FIG. 7] A diagram illustrating an association between a disclosure item and other disclosure items.

[FIG. 12] A diagram illustrating an example of conditions set for respective disclosure items.

DESCRIPTION OF EMBODIMENTS

1. Embodiment

An embodiment of the present invention will be described below in detail with reference to the accompanying drawings. An information processing device according to the present invention is applicable to various computers, such as a personal computer, a mobile phone (smartphone), and a personal digital assistance (PDA) device. In the following embodiment, an insurance contract system including the information processing device according to the present invention will be discussed.

2. Hardware Configuration of Insurance Contract System

Figure 1:
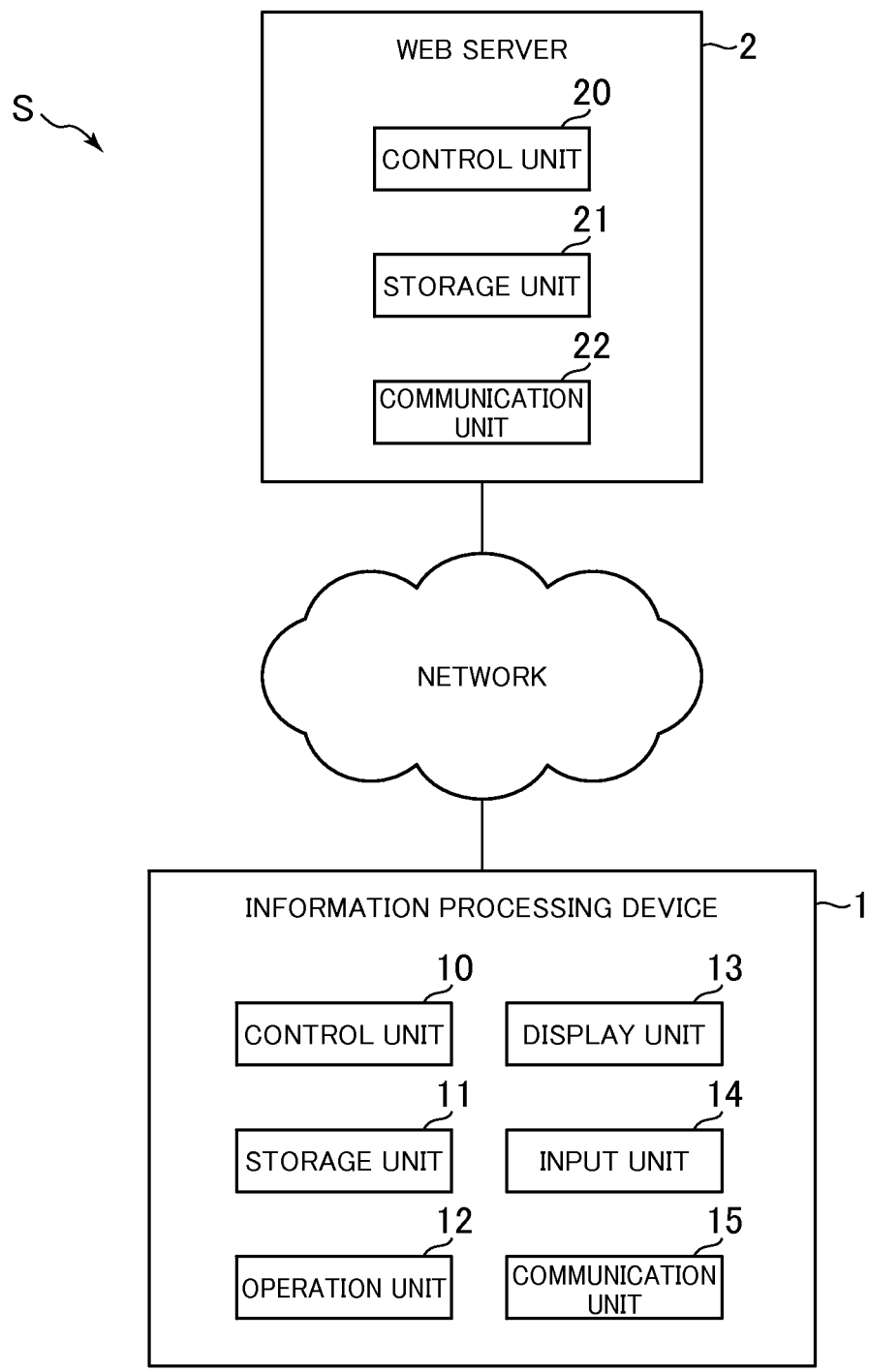
[FIG. 1] A diagram illustrating overall configuration of an insurance contract system.

FIG. 1 illustrates overall configuration of the insurance contract system. As shown in FIG. 1, the insurance contract system S includes an information processing device 1 and a web server 2. The devices included in the insurance contract system S are connected to one another via a network so that data communication is available.

The information processing device 1 includes a control unit 10, a storage unit 11, an operation unit 12, a display unit 13, an input unit 14, and a communication unit 15. The information processing device 1 may include other components that are not shown.

The control unit 10 includes, for example, a CPU. The control unit 10 executes a program stored in the storage unit 11 to perform various processing, and sends and receives data to and from the information processing device 1 through the communication unit 15. The storage unit 11 includes, for example, a hard disk and a memory such as a RAM. The storage unit 11 stores various programs, such as a game program, and various data.

The operation unit 12 includes a mouse and a keyboard, for example, and transmits user's operation to the control unit 10. The display unit 13 includes a liquid crystal display panel, and displays various screens in response to an instruction from the control unit 10. The input unit 14 includes a DVD player, and inputs various data from an external storage device. The communication unit 15 is, for example, a communication device such as a network card.

The web server 2 is, for example, a known server computer. For example, the web server 2 sends HTML data to the information processing device 1 in response to a request from the information processing device 1. The information processing device 1 displays various screens on the display unit 13 based on the HTML data received from the web server 2, and executes JavaScript (registered trade mark) included in the HTML data.

The web server 2 includes a control unit 20, a storage unit 21, and a communication unit 22. The explanation of the control unit 20, the storage unit 21, and the communication unit 22 will be omitted because they have the same hardware configuration as the control unit 10, the storage unit 11, and the communication unit 15, respectively. Here, the storage unit 21 is a computer-readable information storage medium for storing HTML data, for example, and the communication unit 15 functions as means for sending HTML data including JavaScript to the information processing device 1. The web server 2 may include a keyboard, a monitor, and a reader of an information storage medium, which are not shown.

The information processing device 1 of the insurance contract system S displays a Web page on a Web browser in order for a user to apply for an insurance contract based on the HTML data received from the web server 2. The user applies for the insurance contract by entering information on the Web page. The insurance for which the user applies is applicable to various types of known insurance, such as, life insurance, medical insurance, health insurance, cancer insurance, and death insurance.

For example, the user applies for an insurance contract according to the steps described below. When the user follows the steps 1 to 5 below in order, information entered from the Web browser is sent to the web server 2, and the application for the insurance contract is completed.

(Step 1) input personal information of a policyholder (insured), such as a name and an address.
(Step 2) check important matters, such as terms of the contract.
(Step 3) input various disclosure statements relating to health condition of the policyholder.
(Step 4) select a payment method of insurance fee.
(Step 5) make a final review of the input information.

The disclosure statement is information on past and current injury and disease (including disorder and aftereffect) history or examinations of the policyholder. The disclosure statement that the user needs to input includes several questions, for example, an injury/disease or examination name of the policyholder, a treatment period of the injury/disease or an examination period, current condition of the injury/disease or the examination, details of the treatment or examination of the injury/disease, a medical institution name that has provided the treatment or examination, and details of the injury/disease. The user who inputs the disclosure statement on the Web browser may be the same person as the policyholder or the different person.

FIG. 2 illustrates an example of a disclosure statement input screen for a user to input disclosure statement. As shown in FIG. 2, the disclosure statement input screen 30 includes questions 31A-31H (hereinafter, simply referred to as questions 31) regarding the health condition of the policyholder, radio buttons 32A-32H (hereinafter, simply referred to as radio buttons 32) for the user to select answers for the questions.

The questions 31 relate to, for example, whether the policyholder has an injury/disease or an examination. Here, the user moves a cursor C to answer the questions 31, thereby inputting each item of the disclosure statement. The radio buttons 32 are used for the user to select answers for the questions 31. If a radio button 32 indicating "Yes" is selected for an answer for a question 31, the disclosure statement input screen 30 displays an input form to which the user inputs items of the disclosure statement (a type of the disclosure statement that the user needs to disclose) relating to the questions 31.

FIG. 3 illustrates an example of the disclosure statement input screen 30 in a case where the radio button 32A indicating "Yes" is selected. As shown in FIG. 3, the question 31A includes multiple disclosure items, and an input form for the user to input each of the items of the disclosure statement is displayed. The disclosure item is an item that the user needs to disclose regarding the health condition of the policyholder, and each of the questions 31 includes multiple disclosure items. If the user selects a radio button 32A indicating "NO", these input forms are not displayed.

An input form 33A is an area for receiving the input of the user regarding the injury/disease name or the examination name of the policyholder. For example, the user operates the operation unit 12 to input a character string indicating the policyholder's past and current injury/disease name or examination name into the name input form 33A. In this regard, candidates of the injury/disease name or examination name may be included in HTML data, and the user may select the injury/disease name or the examination name from, for example, a pull-down menu.

A period input form 34A is an area for receiving the input of the user regarding the policyholder's treatment period of the injury/disease or the examination period. For example, the user operates the operation unit 12 to select a treatment period or an examination period from the pull-down menus in the period input form 34A, thereby inputting the treatment period or the examination period in the period input form 34A. The values displayed in the pull-down menus are included in the HTML data. Alternatively, without use of the pull-down menu, the value may be input into the period input form 34A directly by the user.

A condition input form 35A is an area for receiving the input of the user regarding a current condition of the injury/disease or the examination of the policyholder. Here, multiple types of conditions (in FIG. 3, three types of conditions "fully-healed", "under treatment" and "follow-up") are prepared in advance. The condition input form 35A is an area for the user to select one of the multiple conditions. For example, the user operates the operation unit 12 to select one of the radio buttons in the condition input form 35A, thereby inputting the current condition of the policyholder's injury/disease or examination. In this regard, a checkbox may be used instead of a radio button, and a character string may be input in the condition input form 35A directly by the user.

A treatment/examination input form 36A is an area for receiving the input of the user regarding treatment or examination of the policyholder. Multiple options of treatments and examinations (in FIG. 3, five types of options "examination/consultation/interview", "medication", "hospital visit", "hospitalization", and "surgery") are prepared in advance. The treatment/examination input form 36A is an area for the user to select any of the options for the treatment or the examination. For example, the user operates the operation unit 12 to select at least one of the checkboxes in the treatment/examination input form 36A, thereby inputting the detail of the policyholder's treatment or examination. Here, a radio button may be used instead of a checkbox, and a character string may be input into the treatment/examination input form 36A directly by the user.

A medical institution input form 37A is an area for receiving the input of the user regarding a name of medical institution where the policyholder underwent the treatment or the examination. For example, the user operates the operation unit 12 to input a character string indicating the name of medical institution into the medical institution input form 37A.

A treatment/examination detail input form 38A is an area for receiving the input of the user regarding details of treatment or examination of the policyholder. For example, the user operates the operation unit 12 to input a character string indicating the details of the treatment or the examination of the policyholder in the medical institution input form 37A. Information that is input in the medical institution input form 37A includes causes or symptoms of the injury/disease of the policyholder, reasons and progress of the examination, current condition, and a name of medicine if any medication.

When the user finishes inputting the disclosure statement for each of the disclosure items of the questions 31A, the user selects a radio button 32B corresponding to the subsequent question 31B, and inputs the answer for question 31B. In the same way as mentioned above, when a radio button 32B indicating "Yes" to the question 31B is selected, the disclosure statement input screen 30 displays various input forms to which the user inputs items of the disclosure statement.

FIG. 4 illustrates an example of the disclosure statement input screen 30 in a case where a radio button 32B indicating "Yes" is selected. As shown in FIG. 4, similarly to FIG. 3, a name input form 33B, a period input form 34B, a condition input form 35B, a treatment/examination input form 36B, a medical institution input form 37B, and a treatment/examination detail input form 38B are displayed when the user inputs the disclosure statement for the question 31B. If the user selects a radio button 32B indicating "NO", these input forms are not displayed.

As shown in FIG. 4, the disclosure items regarding the question 31A and the disclosure items regarding the question 31B are related to each other, and the user answers to the same types of the questions. Here, the question 31A and the question 31B are both the disclosure items related to, for example, the recent injury/disease of the policyholder. As such, it is highly likely that the user inputs the same disclosure statement into, for example, the name input form 33B. In this embodiment, when the user moves a cursor C to focus on the name input form 33B, for example, it is possible to take over content from the disclosure statement input in the name input form 33A, for example.

FIG. 5 illustrates an example of the disclosure statement input screen 30 when the name input form 33B is focused. As shown in FIG. 5, a menu 39 is displayed near the name input form 33B. The menu 39 displays the disclosure statement that the user has already input in response to the question 31A.

Here, the name input form 33A and the name input form 33B are the disclosure items related to each other, and thus the menu 39 displays the disclosure statement (here, injury/disease name or examination name) that the user has input in the name input form 33A. When the disclosure statement displayed on the menu 39 is selected, the selected disclosure statement is input in the name input form 33B.

Similarly, when the user moves the cursor C to focus on the medical institution input form 37B or the treatment/examination detail input form 38B, the menu 39 displays the disclosure statement that the user has input in the medical institution input form 37A or the treatment/examination detail input form 38A. When the user selects the disclosure statement displayed on the menu 39, the selected disclosure statement is input in the medical institution input form 37B or the treatment/examination detail input form 38B.

As described above, in the insurance contract system S of this embodiment, when the user inputs a disclosure statement into an input form of a disclosure item, such input form takes over the disclosure statement input in the input form of another disclosure item related to the disclosure item input by the user, so as to reduce a burden on a user when inputting information. In the following, details of this technology will be discussed.

3. Functions Implemented by Information Processing Device

Figure 6:
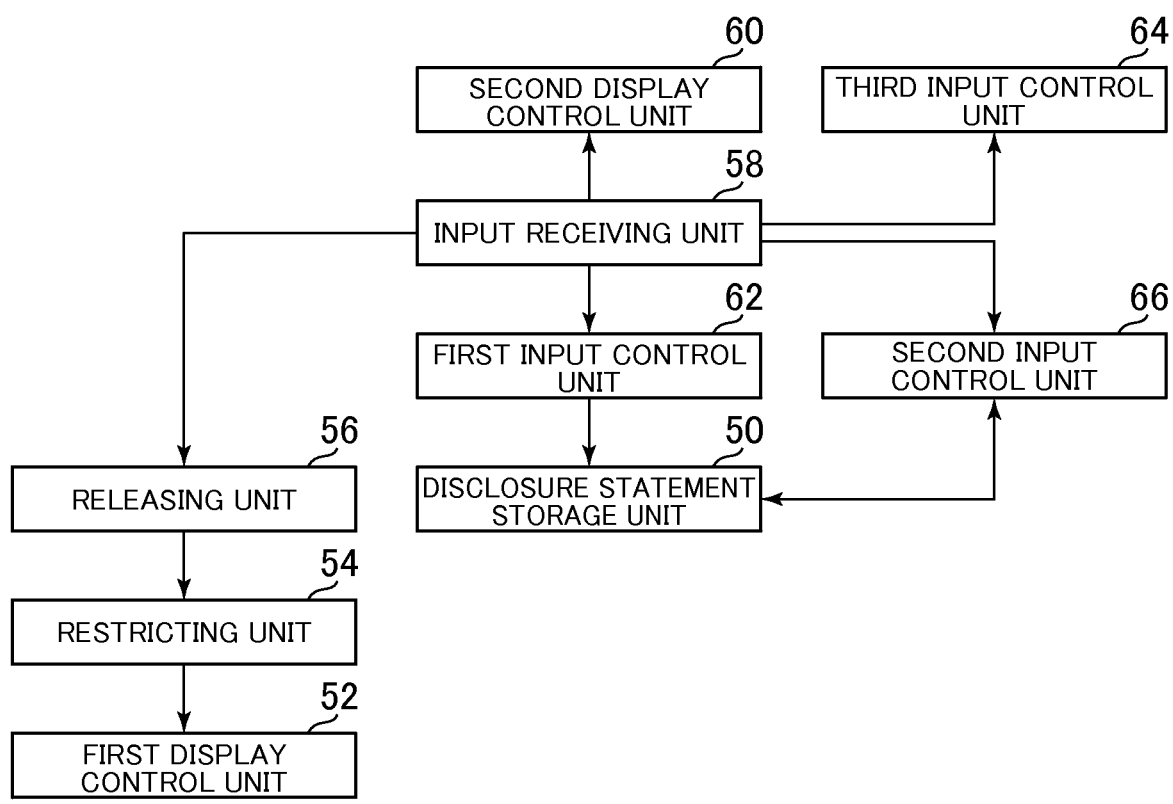
[FIG. 6] A block diagram illustrating functions implemented by an information processing device.

FIG. 6 is a block diagram illustrating functions implemented by the information processing device 1. As shown in FIG. 6, the information processing device 1 implements a disclosure statement storage unit 50, a first display control unit 52, a restricting unit 54, a releasing unit 56, an input receiving unit 58, a second display control unit 60, a first input control unit 62, a third display control unit 64, and a second input control unit 66.

The functions shown in FIG. 6 are implemented by the control unit 10 that operates according to the program read from the storage unit 11 and the JavaScript described in the HTML data received from the web server 2. The disclosure statement storage unit 50 is mainly implemented by the storage unit 11, and other functions are mainly implemented by the control unit 10. In FIG. 6, the essential functions are the first display control unit 52, the input receiving unit 58, the first input control unit 62, the third display control unit 64, and the second input control unit 66. Other functions may be omitted.

3-1. Disclosure Statement Storage Unit

The disclosure statement storage unit 50 stores information on the disclosure statement input by the user. That is, the disclosure statement storage unit 50 stores information input by the user in each input form displayed on the disclosure statement input screen 30. The user's disclosure statement stored in the statement storage unit 50 is sent to the web server 2 at predetermined timing.

3-2. First Display Control Unit

The first display control unit 52 displays input forms (e.g., name input form 33) of multiple disclosure items on the screen (e.g., disclosure statement input screen 30). The input form is an area on the screen for the user to input the disclosure statement, and includes, for example, a text input field in which a user inputs text (character string), a radio button, a checkbox, a pull-down select box, and list-type select box.

3-3. Restricting Unit

The restricting unit 54 restricts a user's input of a disclosure statement in each input form. "Restrict input" means preventing a user's input (input or display) of a disclosure statement in an input form even if the user operates to do so, and includes, for example, hiding a input form temporarily, and restricting focus on input forms.

3-4. Releasing Unit

When releasing operations associated with respective disclosure items are performed, releasing unit 56 releases restriction of input of the disclosure items in the input forms.

Releasing operation is a predetermined operation set for each disclosure item. In this embodiment, to select a radio button 32 indicating "Yes" as an answer for each of questions 31 corresponds to the releasing operation.

"Releases restriction of input of the disclosure items in the input forms" means enabling input of the disclosure statement in input forms in response to the user's operation, and includes, for example, displaying a hidden input form on the screen, and permitting focus on the input forms. In this embodiment, when a radio button 32 indicating "Yes" to a question 31 is selected, the releasing unit 56 displays, for example, the name input form 33 that has been hidden on the disclosure statement input screen 30.

3-5. Input Receiving Unit

The input receiving unit 58 receives input of a disclosure statement by the user in each input form (e.g., name input form 33). The input receiving unit 58 receives input of text in a text input field, selection of a radio button, selection of a checkbox, or selection of a select box based on a detection signal from the operation unit 12.

3-6. Second Display Control Unit

When the user inputs a disclosure statement into one of the input forms (e.g., name input form 33) of the disclosure items, the second display control unit 60 displays a plurality of disclosure statement candidates on a screen (e.g., disclosure statement input screen 30).

"When the user inputs a disclosure statement" is when the user selects the input form, or when the user is allowed to input in the input form, i.e., the input form is focused. For example, a case where the user moves a cursor over the input form or selects a pull-down menu of the select box corresponds a case where the user inputs a disclosure statement.

The disclosure statement candidate is a candidate of the disclosure statement that the user should input. For example, the disclosure statement candidate includes a symbol string (character string or numerical string) to be input as a disclosure statement, or an item to be selected by the user. The disclosure statement candidate is included in, for example, HTML data. For example, a radio button or a symbol string indicated along with the checkbox, or a symbol string displayed in the select box corresponds to the disclosure statement candidate. The second display control unit 60 displays a plurality of disclosure statement candidates included in the HTML data of the disclosure statement input screen 30 on the disclosure statement input screen 30.

In this embodiment, the input receiving unit 58 receives inputs of the disclosure statement regarding given disclosure items (e.g., treatment period of injury/disease or examination period of examination) from the user by receiving the user's select from the disclosure statement candidates. That is, the input receiving unit 58 receives the disclosure statement candidate selected by the user among from disclosure statement candidates displayed on the disclosure statement input screen 30, as the disclosure statement that the user has input.

3-7. First Input Control Unit

The first input control unit 62 inputs the disclosure statement into the input form (e.g., name input form 33) in which the user has input the disclosure statement. "Inputs the disclosure statement" means displaying the disclosure statement on the input form, for example, reflecting (displaying) a symbol string into an input form, and reflecting (displaying) what the user has selected into a radio button, a checkbox, or a select box.

3-8. Third Display Control Unit

When the user inputs a disclosure statement into one of input forms (e.g., name input form 33) of the disclosure items, the third display control unit 64 displays, on the screen (e.g., disclosure statement input screen 30), one or more disclosure statement that the user has input into the input form of one or more other disclosure items associated with the disclosure item.

FIG. 7 is a diagram indicating an association between a disclosure item and other disclosure items. The association shown in FIG. 7 is defined in the HTML data of the disclosure statement input screen 30. Here, the disclosure items are divided into some groups according to nature (type) of disclosure items, and each group has one or more disclosure items. The disclosure items belonging to the same group are the disclosure items associated with one another.

The third display control unit 64 refers to the association defined in the HTML data, and specifies the other disclosure items associated with the disclosure item to be input by the user. Subsequently, the third display control unit 64 refers to the disclosure statement storage unit 50, obtains the disclosure statement that has been input in the specified disclosure items, and displays the obtained disclosure statement on the menu 39. For example, if there are some disclosure items associated with the disclosure item to be input, and disclosure statements are respectively input in input forms of these disclosure items, the third display control unit 64 makes a list of the input disclosure statements and displays the list in the menu 39.

In this case, the input receiving unit 58 receives the disclosure statements that are displayed in the menu 39 and selected by the user. The input receiving unit 58 receives at least one selection of the disclosure statements displayed in the menu 39 based on the operation signal from the operation unit 12.

3-9. Second Input Control Unit

When the user inputs a disclosure statement into one of input forms (e.g., name input form 33B) of the disclosure items, the second input control unit 66 inputs, into the input form, the disclosure statement entered by the user in the input form (e.g., name input form 33A) of another disclosure item associated with the disclosure item. The second input control unit 66 refers to the disclosure statement storage unit 50 to obtain the disclosure statement that is input in another disclosure item associated with the disclosure item to be input, and inputs the obtained disclosure statement into the input form of the disclosure item to be input.

In this embodiment, the second input control unit 66 inputs the disclosure statement, which is displayed in the menu 39 and selected by the user, into the input form of the disclosure item to be input. The second input control unit 66 inputs, into this input form, the disclosure statement selected by the user from the disclosure statements displayed in the menu 39.

4. Processing Executed in Information Processing Device

Figure 8:
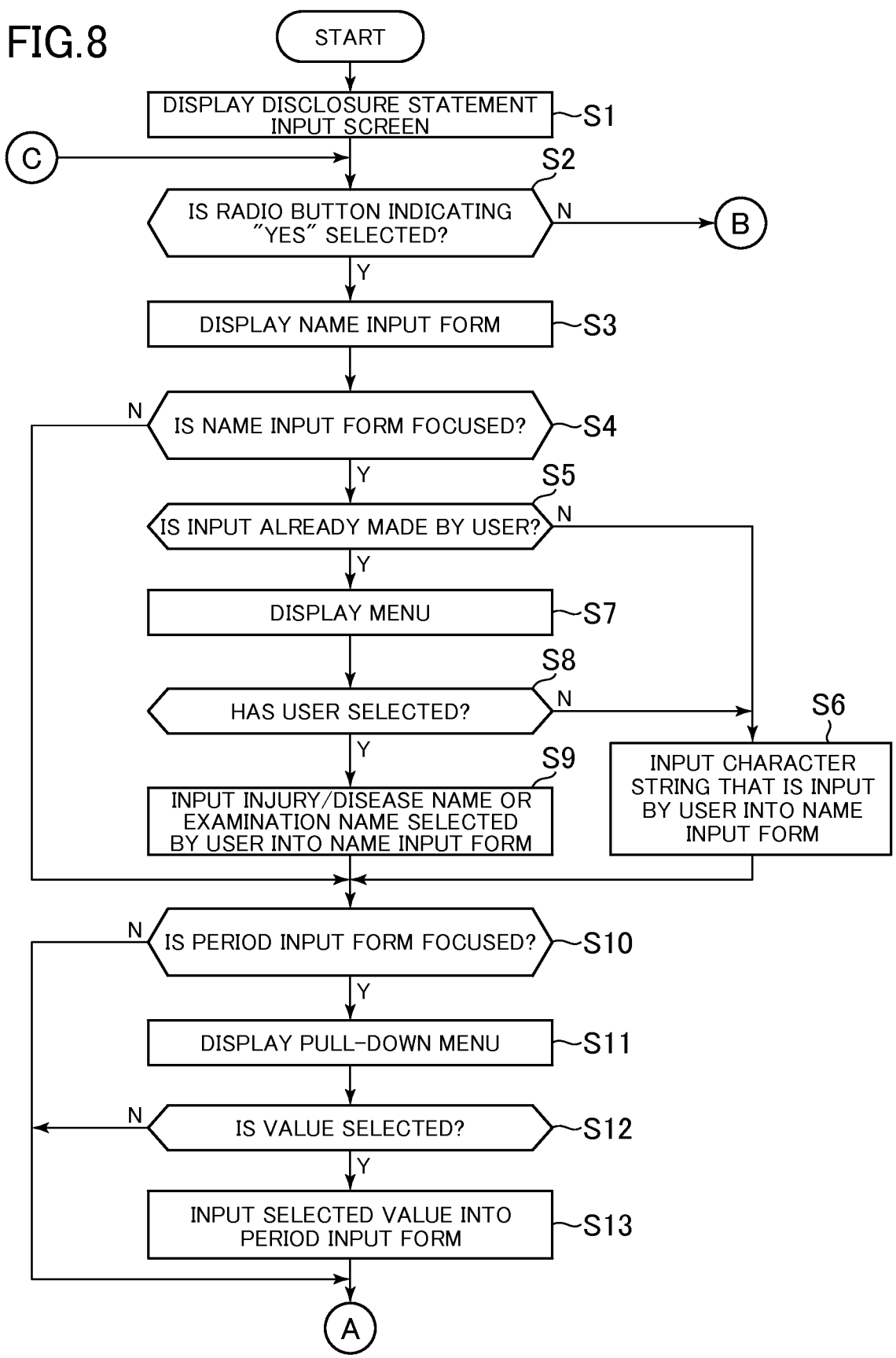
[FIG. 8] A flow chart illustrating an example of processing executed in the information processing device.
Figure 9:
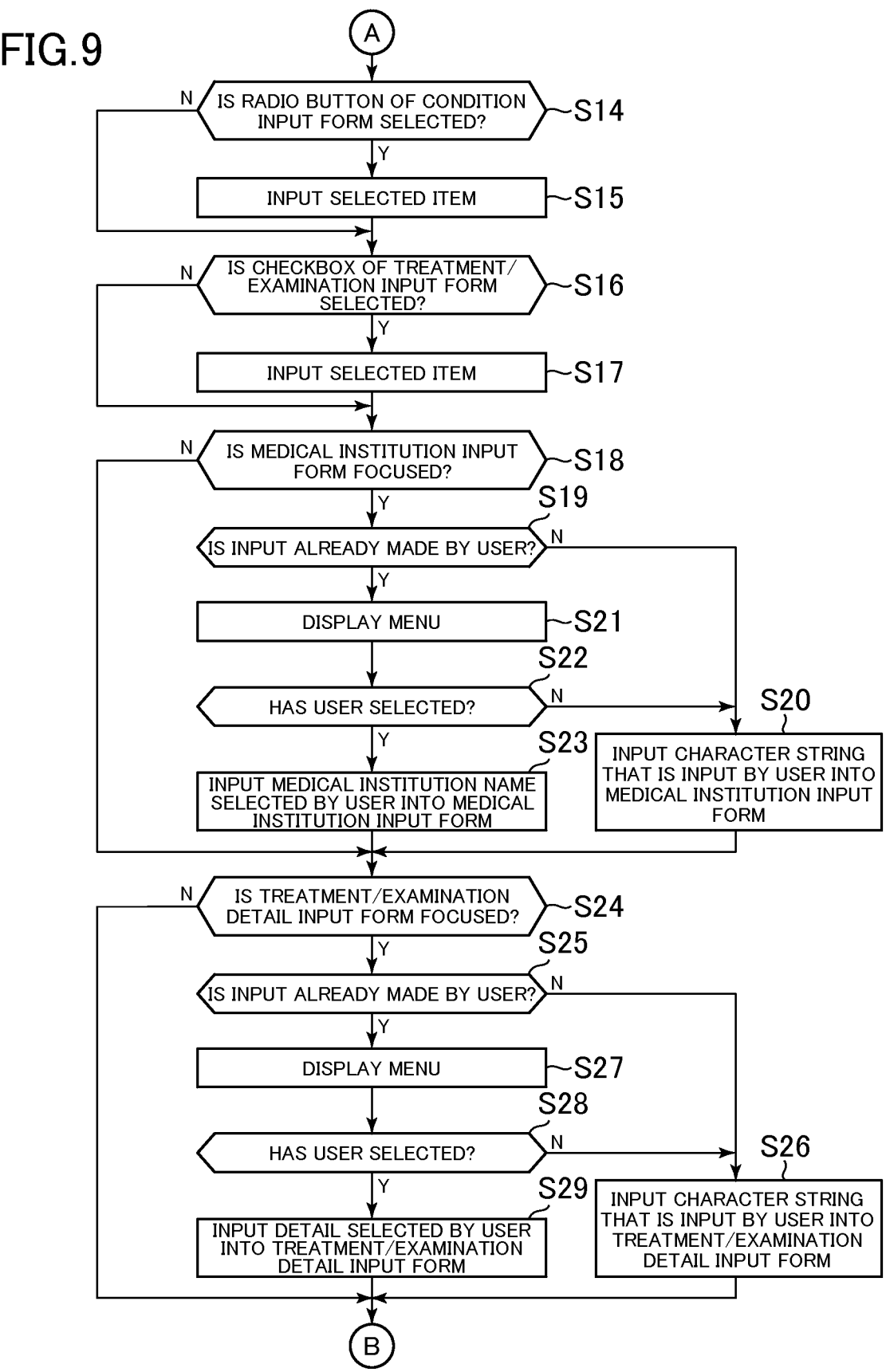
[FIG. 9] A flow chart illustrating an example of processing executed in the information processing device.
Figure 10:
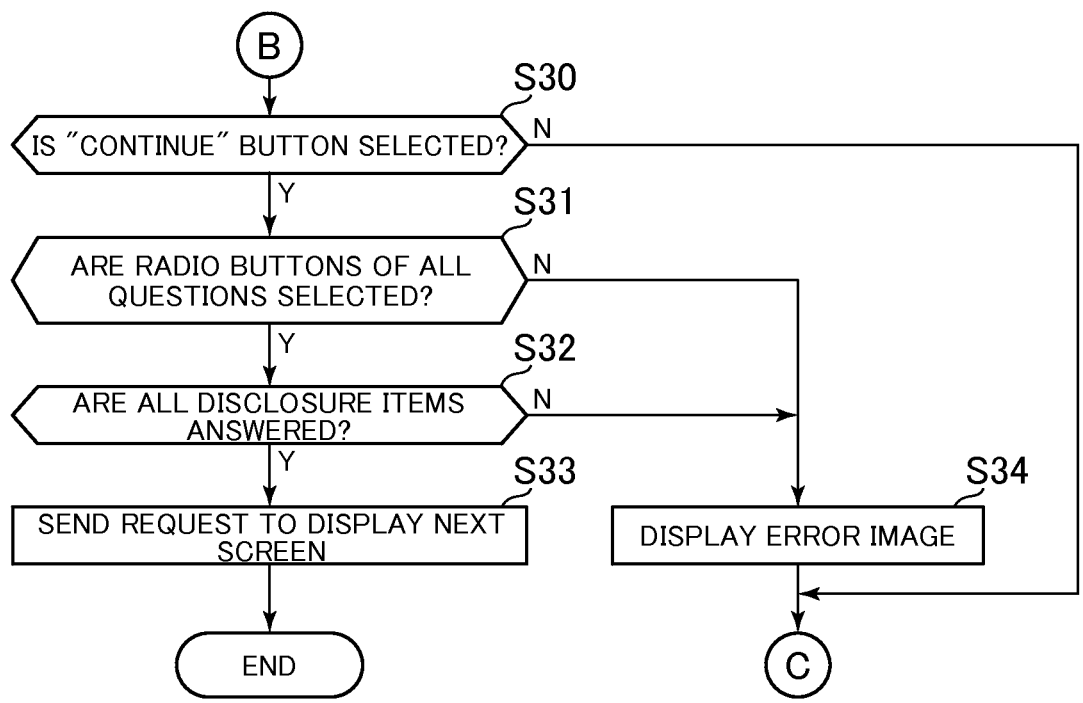
[FIG. 10] A flow chart illustrating an example of processing executed in the information processing device.

FIGS. 8-10 are flow diagrams illustrating examples of processing executed in the information processing device 1. The processing shown in FIGS. 8-10 is executed by the control unit 10 that operates according to a program read from the storage unit 11 and a program obtained from the web server 2. The processing in FIGS. 8-10 is executed when the information processing device 1 receives HTML data of the disclosure statement input screen 30 from the web server 2.

As shown in FIG. 8, the control unit 10 displays the disclosure statement input screen 30 on the display unit 13 based on the HTML data received from the web server 2 (S1). The HTML data of the disclosure statement input screen 30 includes JavaScript, for example, data to define association between a plurality of disclosure items and data indicative of a plurality of disclosure statement candidates. The processing described below is executed by the control unit 10 that executes the JavaScript.

In S1, the disclosure statement input screen 30 as shown in FIG. 2 is displayed on the display unit 13. In this state, the radio button 32 is not selected yet, and, for example, the name input forms 33 corresponding to respective questions 31 are hidden. This means that the user's input to the name input form 33, for example, is restricted.

The control unit 10 determines whether or not the radio buttons 32 indicating "Yes" as an answer to the question 31 is selected, based on the operation signal from the operation unit 12 (S2). If it is determined that the radio button 32 indicating "Yes" is selected (S2;Y), the control unit 10 displays, for example, the name input form 33 on the disclosure statement input screen 30 (S3). In S3, focus on the name input forms 33, for example, is available, and thus the restriction on the user's input in the name input forms 33 is released. The storage unit 11 stores information for identifying the radio button 32 selected by the user.

The control unit 10 determines whether or not the name input form 33 is focused based on the operation signal from the operation unit 12 (S4). If it is determined that the name input form 33 is focused (S4;Y), the control unit 10 refers to stored content of the storage unit 11, and determines whether or not the user has already input an injury/disease name or an examination name in another name input form 33 (S5).

If it is determined that the user has not input an injury/disease name or an examination name in another name input form 33 (S5;N), the control unit 10 inputs the character string, which the user inputs by the operation unit 12, into the name input form 33 (S6). In S6, the control unit 10 temporarily stores the character string, which the user has input into the name input form 33, in the storage unit 11, and displays the character string in the focused name input form 33.

On the other hand, if it is determined that the user has already input an injury/disease name or an examination name in another name input form 33 (S5;Y), the control unit 10 generates a menu 39 including the injury/disease name or the examination name that has been input on the disclosure statement input screen 30 (S7).

The control unit 10 determines whether or not the user has selected the injury/disease name or examination name displayed on the menu 39 based on the operation signal from the operation unit (S8). If it is determined that the user selects the injury/disease name or the examination name displayed on the menu 39 (S8;Y), the control unit 10 inputs the selected injury/disease name or examination name into the name input form 33 (S9). In S9, the control unit 10 temporarily stores the character string, which indicates the injury/disease name or the examination name selected by the user, in the storage unit 11 as the character string that has been input in the focused name input form 33, and displays the character string on the focused name input form 33.

On the other hand, if it is not determined that the user has selected the injury/disease name or the examination name displayed on the menu 39 (S8;N), the processing proceeds to S6.

The control unit 10 determines whether or not the period input form 34 is focused based on the operation signal from the operation unit 12 (S10). If it is determined that the period input form 34 is focused (S10; Y), the control unit 10 displays values (disclosure statement candidate) described in the HTML data on the pull-down menu of the period input form 34 (S11). In S11, the control unit 10 displays a list of values indicating, for example, year, month, and day on the pull-down menu of the period input form 34.

The control unit 10 determines whether or not the value displayed on the pull-down menu of the period input form 34 is selected based on the operation signal of the operation unit 12 (S12). If it is determined that the value displayed on the pull-down menu is selected (S12; Y), the control unit 10 inputs the selected value into the period input form 34 (S13). In S13, the control unit 10 temporarily stores the value, which is selected by the user from the pull-down menu of the period input form 34, in the storage unit 11, and displays the value on the focused period input form 34.

Referring to FIG. 9, the control unit 10 determines whether or not a radio button of the condition input form 35 is selected based on the operation signal from the operation unit 12 (S14). If it is determined that the radio button in the condition input form 35 is selected (S14; Y), the control unit 10 inputs an item corresponding to the selected radio button into the condition input form 35 (S15). In S15, the control unit 10 temporarily stores information, which identifies the radio button selected by the user in the condition input form 35, in the storage unit 11, and displays the selected radio button on the focused condition input form 35 as the selected radio button.

The control unit 10 determines whether or not a checkbox of the treatment/examination input form 36 is selected based on the operation signal of the operation unit 12 (S16). If it is determined that the checkbox of the treatment/examination input form 36 is selected (S16;Y), the control unit 10 inputs an item corresponding to the selected checkbox into the treatment/examination input form (S17). In S17, the control unit 10 temporarily stores information, which identifies the checkbox selected by the user in the treatment/examination input form 36, in the storage unit 11, and displays the selected checkbox on the focused treatment/examination input form 36 as the selected checkbox.

The control unit 10 determines whether or not the medical institution input form 37 is focused (S18). If it is determined that the medical institution input form 37 is focused (S18;Y), the control unit 10 refers to the stored content of the storage unit 11, and determines whether or not the user has already input a name of the medical institution into another medical institution input form 37 (S19).

If it is determined that the user has not input the name of the medical institution in another medical institution input form 37 (S19;N), the control unit 10 inputs the character string, which is input from the operation unit 12, into the medical institution input form 37 (S20). In S20, the control unit 10 temporarily stores the character string, which is input by the user to the medical institution input form 37, in the storage unit 11, and displays the character string on the focused medical institution input form 37.

On the other hand, if it is determined that the user has already input the name of the medical institution into another medical institution input form 37 (S19;Y), the control unit 10 generates a menu 39 including the name of the medical institution that has been input, and displays the generated menu 39 on the disclosure statement input screen 30 (S21).

The control unit 10 determines whether or not the name of the medical institution displayed on the menu 39 is selected by the user based on the operation signal from the operation unit 12 (S22). If it is determined that the name of the medical institution displayed on the menu 39 is selected by the user (S22;Y), the control unit 10 inputs the selected name of the medical institution into the medical institution input form 37 (S23). In S23, the control unit 10 temporarily stores the character string, which indicates the name of the medical institution selected by the user, in the storage unit 11 as the character string that has been input in the focused medical institution input form 37, and displays the character string on the focused medical institution input form 37.

On the other hand, if it is not determined that the name of the medical institution displayed on the menu 39 is selected (S22;N), the processing proceeds to S20.

The control unit 10 determines whether or not the treatment/examination detail input form 38 is focused (S24). If it is determined that the treatment/examination detail input form 38 is focused (S24;Y), the control unit 10 refers to the stored content in the storage unit 11, and determines whether or not the user has already input a detail of the injury/disease or the examination into another treatment/examination detail input form 38 (S25).

If it is determined that the user has not input the detail of the injury/disease or the examination in another treatment/examination detail input form 38 (S25;N), the control unit 10 inputs the character string, which is input from the operation unit 12, into the treatment/examination detail input form (S26). In S26, the control unit 10 temporarily stores the character string, which is input by the user into the treatment/examination detail input form 38, in the storage unit 11, and displays the character string on the focused treatment/examination detail input form 38.

On the other hand, if it is determined that the user has already input the detail of the injury/disease or the examination into another treatment/examination detail input form 38 (S25;Y), the control unit 10 generates a menu 39 including the detail of the injury/disease or the examination that has been input, and displays the generated menu on the disclosure statement input screen 30 (S27).

The control unit 10 determines whether or not the detail of the injury/disease or the examination displayed on the menu 39 is selected by the user based on the operation signal from the operation unit 12 (S28). If it is determined that the detail of the injury/disease or the examination displayed on the menu 39 is selected by the user (S28;Y), the control unit 10 inputs the detail of the selected injury/disease or examination into the treatment/examination detail input form 38 (S29). In S29, the control unit 10 temporarily stores the character string, which indicates the detail of the injury/disease or the examination selected by the user, in the storage unit 11 as the character string that is input into the focused treatment/examination detail input form 38, and displays the character string on the focused treatment/examination detail input form 38.

On the other hand, if it is not determined that the detail of the injury/disease or the examination displayed on the menu 39 is selected (S28;N), the processing proceeds to S26.

Referring to FIG. 10, the control unit 10 determines whether or not a "Continue" button 40 is selected (S30). If it is determined that the "Continue" button 40 is selected (S30;Y), the control unit 10 refers to the stored content of the storage unit 11, and determines whether or not the radio buttons 32 of all of the questions 31 are selected (S31).

If it is determined that all of the radio buttons 32 are selected (S31;Y), the control unit 10 refers to the stored content of the storage unit 11, and determines whether or not all of the disclosure items are answered (S32). In S32, the control unit 10 determines whether or not the user has input the disclosure statements of all of the disclosure items.

If it is determined all of the disclosure items are answered (S32;Y), the control unit 10 sends a request to the web server 2 to display a next screen (S33), and the processing is finished. The disclosure statements stored in the storage unit 11 are sent to the web server 2 at a predetermined timing.

On the other hand, if it is determined that there is a radio button 32 that is not selected (S31;N), and there is a disclosure item that is not answered (S32;N), the control unit 10 displays an error image on the display unit 13 (S34), and the processing returns to S2. In this case, input of a disclosure item to which the user has not input a disclosure statement is accepted.

According to the insurance contract system S described above, in a case where the user answers a disclosure statement to one of the questions 31, the user's burden can be reduced by taking over the disclosure statement that has been input in another question 31. Further, when the disclosure statement that has been input in another question 31 is taken over, the user can select one of the disclosure statements displayed on the menu 39.

5. Variations

The present invention is not to be limited to the above described embodiment and can be changed as appropriate without departing from the spirit of the invention.

Figure 11:
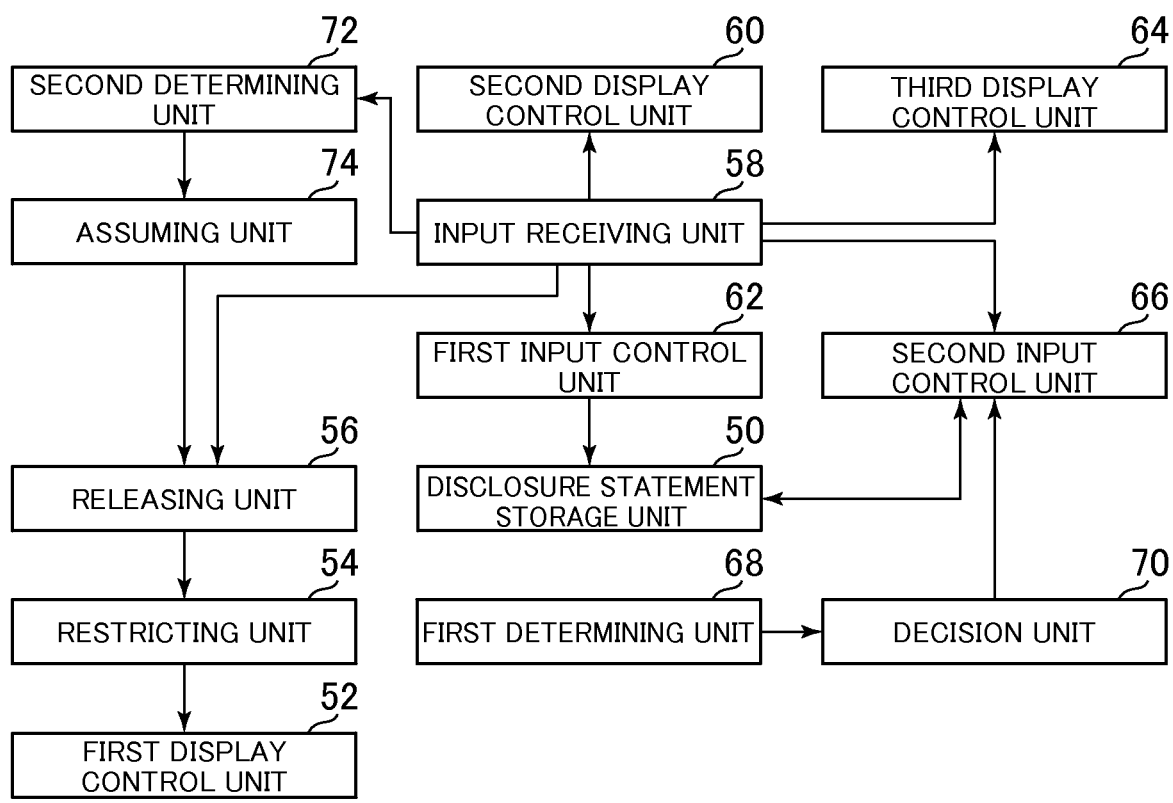
[FIG. 11] A functional block diagram of a variation.

FIG. 11 is a functional block diagram of a variation. As shown in FIG. 11, in a variation, a first determining unit 68, a decision unit 70, a second determining unit 72, and an assuming unit 74 are implemented in addition to the functions of the embodiment. These functions are mainly implemented by the control unit 10.

(1) For example, the HTML data of the disclosure statement input screen 30 may include a JavaScript different for each of the questions 31, and the processing for taking over the disclosure statement to the input form on which the user focuses may be different for each of the questions 31. In other words, only when a disclosure statement input into an input form of a disclosure item satisfies a predetermined condition, such disclosure statement may be taken over to an input form of another disclosure item.

FIG. 12 illustrates an example of conditions determined for each disclosure item. As shown in FIG. 12, in the variation (1), each disclosure item sets a condition regarding the disclosure statement that is input into other disclosure items. When a condition set for a certain disclosure item is satisfied, the disclosure statement of another disclosure item is taken over to such disclosure item. This condition is a condition indicative of whether or not a health condition of a policyholder is a given status, and whether or not the disclosure statement of another disclosure item has given content.

(1-1) For example, the question 31B relates to hospitalization. If the user has not selected a checkbox for "hospitalization" in the treatment/examination input form 36A of the question 31A, it is not necessary to take over the disclosure statement that has been input into the question 31A to the disclosure item of the question 31B. As such, whether or not to take over the disclosure statement may be determined according to the treatment or the examination that the user has input.

The information processing device 1 of the variation (1-1) includes the first determining unit 68 and the decision unit 70. When the user inputs a disclosure statement into any one of the input forms of the disclosure items, the first determining unit 68 determines whether or not the disclosure statement input into the input form of another disclosure item associated with the disclosure item to be input by the user relates to the disclosure item to be input by the user.

The first determining unit 68 determines whether or not the treatment of the injury/disease or the examination, which is input into the input form of another disclosure item associated with the disclosure item to be input, relates to the disclosure item to be input. "Relates to the disclosure item to be input" means relating to a given type of treatment or a given type of examination, and relating to a treatment or an examination of the question 31 to be input.

Here, the first determining unit 68 refers to the stored content of the disclosure statement storage unit 50, and specifies the treatment or the examination of the injury/disease relating to another disclosure item associated with the disclosure item to be input. The first determining unit 68 compares the specified treatment or examination with the condition set for the disclosure item to be input (conditions shown in FIG. 12).

For example, if the disclosure item relates to hospitalization of the policyholder as the question 31B, a given treatment or a given examination is hospitalization. For example, if the disclosure item relates to an operation of the policyholder as the question 31C, a given treatment or a given examination is operation. Further, for example, if the disclosure item relates to an examination of the policyholder as the questions 31D and 31E, a given treatment or a given examination is examination.

The decision unit 70 determines whether or not to execute the processing by the second input control unit 66 based on the determining result of the first determining unit 68. The decision unit 70 determines to execute the processing by the second input control unit 66 when it is determined that the disclosure statement input into the input form of another disclosure item relates to the disclosure item to be input, and determines not to execute the processing by the second input control unit 66 when it is determined that the disclosure statement input into the input form of another disclosure item does not relate to the disclosure item to be input. "Not to execute the processing by the second input control unit 66" means that the second input control unit 66 restricts (prevents) an input of a disclosure statement into an input form.

According to the variation (1), it is possible to prevent the disclosure statement relating to the injury/disease or the examination, which has less relationship with the disclosure item to be input, from being taken over.

(1-2) For example, the question 31H relates to cancer, and if the disclosure statement relating to cancer is not input into other questions 31A-31G, the disclosure statements of the questions 31A-31G may not be taken over to the disclosure item of the question 31H. As such, whether or not to take over a disclosure statement may be determined the injury/disease name or the examination name input by the user.

The first determining unit 68 of the variation (1-2) determines whether or not the injury/disease name or the examination name that is input into the input form of another disclosure item associated with the disclosure item to be input is a name relating to the disclosure item to be input. "Name relating to the disclosure item to be input" is a name of the injury/disease or examination relating to the question 31 to be input. For example, if the disclosure item relates to cancer as the question 31H, a name of given injury/disease or examination is a character string of "cancer."

Here, the first determining unit 68 refers to the stored content of the disclosure statement storage unit 50, and specifies the injury/disease name or the examination name relating to another disclosure item associated with the disclosure item to be input. The first determining unit 68 compares the specified injury/disease name or examination name with the condition set for the disclosure item to be input (condition shown in FIG. 12). For example, such comparing processing is processing for determining a matching (including prefix matching and postfix matching) with a specific character string (e.g., "cancer").

The decision unit 70 determines to execute the processing by the second input control unit 66 when it is determined that the disclosure statement input into the input form of another disclosure item relates to the disclosure item to be input, and determines not to execute the processing by the second input control unit 66 when it is determined that the disclosure statement input into the input form of another disclosure item does not relate to the disclosure item to be input.

According to the variation (1-2), it is possible to prevent the disclosure statement relating to the injury/disease name or the examination name, which has less relationship with the disclosure item to be input, from being taken over.

(1-3) For example, the question 31B relates to a health condition in the last five years, and if the disclosure statement relating to the health condition in the last five years has not been input for other questions 31, these disclosure statements of other questions 31 may not be taken over to the disclosure item of the question 31B. As such, whether or not to take over a disclosure statement may be determined according to a period relating to the injury/disease or the examination input by the user.

The first determining unit 68 of the variation (1-3) determines whether or not a period of treatment or examination of the injury/disease, which is input into the input form of another disclosure item associated with the disclosure item to be input, is a period relating to the disclosure item to be input. "Period relating to the disclosure item to be input" is a period included in the questions 31 to be input. For example, if a disclosure item relates to a health condition in the last five years as the question 31, a period from five years ago to the present time is a period relating to the disclosure item. Further, for example, if a disclosure item relates to a health condition in the last two years as the question 31D, a period from two years ago to the present time is a period relating to the disclosure item.

Here, the first determining unit 68 refers to the stored content of the disclosure statement storage unit 50, and specifies the period of treatment or examination of the injury/disease relating to another disclosure item associated with the disclosure item to be input. The first determining unit 68 compares the specified period of injury/disease or examination with the condition set for the disclosure item to be input (condition shown in FIG. 12).

The decision unit 70 determines to execute the processing by the second input control unit 66 when it is determined that the period of treatment or examination of the injury/disease that is input into the input form of another disclosure item is a period relating to the disclosure item input, and determines not to execute the processing by the second input control unit 66 when it is determined that the period of treatment or examination of the injury/disease that is input into the input form of another disclosure item is not a period relating to the disclosure item input.

According to the variation (1-3), it is possible to prevent the disclosure statement relating to the period, which has less relationship with the disclosure item to be input, from being taken over.

(2) For example, the pull-down menu displayed on the period input form 34 may preferentially display a period that is input in another disclosure item so that the user can easily select such period.

The second display control unit 60 of the variation (2) preferentially displays a disclosure statement candidate, which is input into the input form of another disclosure item associated with the disclosure item to which the user inputs a disclosure statement, over other disclosure statement candidates. "Preferentially displays" means displaying the disclosure statement candidate in the early order, and placing the disclosure statement candidate to be displayed on the predetermined position.

According to the variation (2), it is possible to preferentially display the disclosure statement candidate that is input into the input form of another disclosure item.

(3) For example, when a radio button 32 is selected to answer to one of the questions 31 on the disclosure statement input screen 30, input of the disclosure statement of the disclosure item relating to the question 31 is allowed, although input of disclosure statements of other disclosure items may be allowed according to the disclosure statement input by the user. When "hospitalization" is selected in the treatment/examination input form 36A, for example, it is highly likely the radio button 32B of "Yes" is selected as an answer to the question 31B. As such, when "hospitalization" is selected in the treatment/examination input form 36A, assuming that the radio button 32B of "Yes" is automatically selected, forms such as the name input form 33B may be displayed.

The insurance contract system S of the variation (3) includes the second determining unit 72 and the assuming unit 74. When the user inputs a disclosure statement into an input form having no restriction of input, the second determining unit 72 determines whether or not the disclosure statement that is input relates to another disclosure item.

"Disclosure statement relates to another disclosure item" means a disclosure statement that is associated with another disclosure item, and should be disclosed in another disclosure item. For example, content relating to other disclosure items includes given injury/disease name or examination name, given period, given condition of the injury/disease or the examination, given treatment or examination, given medical institution name. The content relating to another disclosure item is defined in the JavaScript of the HTML data. The second determining unit 72 compares the disclosure statement input by the user with the content relating to another disclosure item, and determines whether or not they match.

The assuming unit 74 assumes that releasing operation of other disclosure items has been performed based on the result of the determination of the second determining unit 72. "Assumes that releasing operation has been performed" means executing the processing in a case where the releasing operation is performed. In this case, it means restriction of input of disclosure statement is released. When a disclosure statement input by the user matches content of another disclosure item, the assuming unit 74 releases the restriction of input of another disclosure item. According to the variation (3), the user's burden to perform releasing operation of input of a disclosure item can be reduced.

(4) For example, a user may be prompted to input all of the disclosure items, or may not be prompted to input specific disclosure items.

For example, in a case where the disclosure statement input into the name input form 33A is taken over to the name input form 33B, all of the disclosure statements input into other input forms of the question 33A may be taken over to other input forms of the question 33B.

The invention claimed is:
1. An information processing device for receiving input of a statement, comprising:
at least one memory configured to store computer program code; and
at least one processor configured to access said at least one memory, read said computer program code, and operate as instructed by said computer program code, said computer program code including:
display control code configured to cause at least one of said at least one processor to display a plurality of input forms for a plurality of disclosure items on a screen, the plurality of input forms requiring answers to the plurality of disclosure items;
receiving code configured to cause at least one of said at least one processor to receive input of the statement in each of the input forms by a user;
first input control code configured to cause at least one of said at least one processor to, in response to receiving an input of a statement answering a first disclosure item among the plurality of disclosure items, input the statement answering the first disclosure item into an input form for the first disclosure item; and
second input control code configured to cause at least one of said at least one processor to, with respect to an input form for a second disclosure item that is associated with the first disclosure item, input the statement that has been input into the input form for the first disclosure item into the input form for the second disclosure item,
wherein the first disclosure item comprises one or more sub-disclosure items further describing details of the first disclosure item, input forms of the one or more sub-disclosure items being provided in response to the statement answering the first disclosure item indicating that the first disclosure item has a first preset status and not provided in response to the statement answering the first disclosure item indicating that the first disclosure item does not have the first preset status,
wherein processing by the second input control code is conditionally performed based on operations of determining code and execution determination code,
the determining code being configured to cause at least one of said at least one processor to determine, with respect to the input form for the second disclosure item, whether the user has input the statement answering a third disclosure item, included in the one or more sub-disclosure items of the first disclosure item, to indicate that the third disclosure item has a given status, the third disclosure item being provided with a plurality of display items to be selectable by the user, and the given status of the third disclosure item being that one of the plurality of display items, which is preset to have association with the second disclosure item, is selected by the user by the statement answering the third disclosure item; and the execution determination code being configured to cause at least one of said at least one processor to execute the processing by the second input control code based on a determination result of the determining code that the third disclosure item has a second preset status, and to not execute the processing by the second input control code based on the determination result of the determining code that the third disclosure item does not have the second preset status, and wherein the first disclosure item and the second disclosure item are displayed in separate graphical display areas and the plurality of display elements of the third disclosure item are located within a graphical display area of the first disclosure item.

2. The information processing device according to claim 1, further comprising:

statement display code configured to cause at least one of said at least one processor to display on the screen, when the user inputs the statement into one of the input forms of the plurality of disclosure items, one or more statements that have been input into the input forms of one or more other disclosure items associated with a disclosure item; and statement receive code configured to cause at least one of said at least one processor to receive the statement selected by the user among from the displayed statements, wherein the second input control code is further configured to cause at least one of said at least one processor to input into the input form, the statement selected by the user among from the displayed statements.

3. The information processing device according to claim 1, further comprising:

candidate display control code configured to cause at least one of said at least one processor to display, when the user inputs the statement into one of the input forms of the plurality of disclosure items, a plurality of statement candidates on the screen, wherein the receiving code is further configured to cause at least one of said at least one processor to receive the input of the statement from the user by receiving the statement selected by the user from the plurality of statement candidates, and the candidate display control code is further configured to cause at least one of said at least one processor to preferentially display a statement candidate that has been input into the input form of another disclosure item associated with a disclosure item to be input over other statement candidates.

4. The information processing device according to claim 1, wherein the receiving code is further configured to cause at least one of said at least one processor to receive input from the user regarding a treatment or an examination of an injury/disease, and the determining code is further configured to cause at least one of said at least one processor to determine whether the treatment or the examination of the injury/disease that has been input into the input form of another disclosure item associated with a disclosure item to be input relates to the disclosure item to be input.

5. The information processing device according to claim 1, wherein the receiving code is further configured to cause at least one of said at least one processor to receive input from the user regarding a name of an injury/disease or an examination, and the determining code is further configured to cause at least one of said at least one processor to determine whether the name of the injury/disease or the examination that has been input into the input form of another disclosure item associated with a disclosure item to be input is the name relating to the disclosure item to be input.

6. The information processing device according to claim 1, wherein the receiving code is further configured to cause at least one of said at least one processor to receive input from the user regarding a period of a treatment or an examination of an injury/disease, and the determining code is further configured to cause at least one of said at least one processor to determine whether the period of the treatment or the examination of the injury/disease that has been input into the input form of another disclosure item associated with a disclosure item to be input is the period relating to the disclosure item to be input.

7. The information processing device according to claim 1, further comprising:

restriction code configured to cause at least one of said at least one processor to restrict input of statements into respective input forms by the user;

release code configured to cause at least one of said at least one processor to release, when a releasing operation associated with each of the plurality of disclosure items is performed, a restriction of the input into the input form of a disclosure item;

determination relate code configured to cause at least one of said at least one processor to determine, when the user inputs the statement into the input form that is released from the restriction, whether the statement input by the user relates to another disclosure item; and assume code configured to cause at least one of said at least one processor to assume that the releasing operation of the another disclosure item is performed based on the determination result of the determination relate code.

8. The information processing device according to claim 1, wherein the display control code is further configured to cause at least one of said at least one processor to display the plurality of input forms in a same page, the second input control code is further configured to cause at least one of said at least one processor to input the statement into the input form, without accessing a server, the determining code is further configured to cause at least one of said at least one processor to determine whether the user has input the statement answering the third disclosure item, without accessing the server, and the execution determination code is further configured to cause at least one of said at least one processor to execute the processing, without accessing the server.

9. The information processing device according to claim 1, wherein the second disclosure item comprises one or more sub-disclosure items further describing details of the second disclosure item, input forms of the one or more sub-disclosure items of the second disclosure being provided in response to the statement answering the second disclosure item indicating that the second disclosure item has a third preset status and not provided in response to the statement answering the second disclosure item indicating that the second disclosure item does not have the third reset status, and wherein, when the execution determination code causes at least one of said at least one processor to execute the processing by the second input control code, the statement answering the third disclosure item is input into an input form for a corresponding one of the one or more sub-disclosure items of the second disclosure item.

10. A method for controlling an information processing device that receives input of a statement, performed by a computer, the method comprising:

displaying a plurality of input forms for a plurality of disclosure items on a screen, the plurality of input forms requiring answers to the plurality of disclosure items;

receiving input of the statement in each of the input forms by a user;

in response to receiving an input of a statement answering a first disclosure item among the plurality of disclosure items, inputting the statement answering the first disclosure item into an input form for the first disclosure item; and with respect to an input form for a second disclosure item that is associated with the first disclosure item, inputting the statement that has been input into the input form for the first disclosure item into the input form for the second disclosure item, wherein the first disclosure item comprises one or more sub-disclosure items further describing details of the first disclosure item, input forms of the one or more sub-disclosure items being provided in response to the statement answering the first disclosure item indicating that the first disclosure item has a first preset status and not provided in response to the statement answering the first disclosure item indicating that the first disclosure item does not have the first preset status, wherein the inputting the statement that been input into the input form for the first disclosure item into the input form for the second disclosure item is conditionally performed based on:

with respect to the input form for the second disclosure item, determining whether the user has input the statement answering a third disclosure item, included in the one or more sub-disclosure items of the first disclosure item, to indicate that the third disclosure item has a given status, the third disclosure item being provided with a plurality of display elements to be selectable by the user, and the given status of the third disclosure item being that one of the plurality of display elements, which is preset to have association with the second disclosure item, is selected by the user by the statement answering the third disclosure item; and executing inputting of the statement that has been input into the input form for the first disclosure item into the input form for the second disclosure item based on a determination result that the user has answered that the third disclosure item has a second preset status, and not executing the processing of the inputting of the statement that has been input into the input form for the first disclosure item into the input form for the second disclosure item based on the determination result that the user has answered that the third disclosure item does not have the second preset status, wherein the first disclosure item and the second disclosure item are displayed in separate graphical display areas and the plurality of display elements of the third disclosure item are located within a graphical display area of the first disclosure item.

11. The method according to claim 10, further comprising:

displaying, when the user inputs the statement into one of the input forms of the plurality of disclosure items, one or more statements that have been input into the input forms of one or more other disclosure items associated with a disclosure item, on the screen;

receiving the statement selected by the user among from the displayed statements; and inputting, into the input form, the statement selected by the user among from the displayed statements.

12. The method according to claim 10, further comprising:

displaying, when the user inputs the statement into one of the input forms of the plurality of disclosure items, a plurality of statement candidates on the screen, wherein the receiving the input of the statement includes receiving the statement selected by the user from the plurality of statement candidates, and the displaying the plurality of statement candidates includes preferentially displaying a statement candidate that has been input into the input form of another disclosure item associated with a disclosure item to be input over other statement candidates.

13. The method according to claim 10, further comprising:

receiving input from the user regarding a treatment or an examination of an injury/disease; and determining whether the treatment or the examination of the injury/disease that has been input into the input form of another disclosure item associated with a disclosure item to be input relates to the disclosure item to be input.

14. The method according to claim 10, further comprising:

receiving input from the user regarding a name of an injury/disease or an examination; and determining whether the name of the injury/disease or the examination that has been input into the input form of another disclosure item associated with a disclosure item to be input is the name relating to the disclosure item to be input.

15. The method according to claim 10, further comprising:

receiving input from the user regarding a period of a treatment or an examination of an injury/disease; and determining whether the period of the treatment or the examination of the injury/disease that has been input into the input form of another disclosure item associated with a disclosure item to be input is the period relating to the disclosure item to be input.

16. The method according to claim 10, further comprising:

displaying, when the user inputs the statement into one of the input forms of the plurality of disclosure items, a plurality of statement candidates on the screen;

receiving the input of the statement from the user by receiving the statement selected by the user from the plurality of statement candidates; and preferentially displaying a statement candidate that has been input into the input form of another disclosure item associated with a disclosure item to be input over other statement candidates.

17. The method according to claim 10, further comprising:
restricting input of statements into respective input forms by the user;
releasing, when a releasing operation associated with each of the plurality of disclosure items is performed, a restriction of the input into the input form of a disclosure item;
determining, when the user inputs the statement into the input form that is released from the restriction, whether the statement input by the user relates to another disclosure item; and
assuming that the releasing operation of the another disclosure item is performed based on the determination result.

18. A non-transitory computer readable information storage medium having stored thereon a program for causing a computer, which receives input of a statement, to perform a function of: displaying a plurality of input forms for a plurality of disclosure items on a screen, the plurality of input forms requiring answers to the plurality of disclosure items; receiving input of the statement in each of the input forms by a user; in response to receiving an input of a statement answering a first disclosure item among the plurality of disclosure items, inputting the statement answering the first disclosure item into an input form for the first disclosure item; and with respect to an input form for a second disclosure item that is associated with the first disclosure item, inputting the statement that has been input into the input form for the first disclosure item into the input form for the second disclosure item, wherein the first disclosure item comprises one or more sub-disclosure items further describing details of the first disclosure item, input forms of the one or more sub-disclosure items being provided in response to the statement answering the first disclosure item indicating that the first disclosure item has a first preset status and not provided in response to the statement answering the first disclosure item indicating that the first disclosure item does not have the first preset status, wherein the inputting the statement that been input into the input form for the first disclosure item into the input form for the second disclosure item is conditionally performed based on: with respect to the input form for the second disclosure item, determining whether the user has input the statement answering a third disclosure item, included in the one or more sub-disclosure items of the first disclosure item, to indicate that the third disclosure item has a given status, the third disclosure item being provided with a plurality of display elements to be selectable by the user, and the given status of the third disclosure item being that one of the plurality of display elements, which is preset to have association with the second disclosure item, is selected by the user by the statement answering the third disclosure item; and executing inputting of the statement that has been input into the input form for the first disclosure item into the input form for the second disclosure item based on a determination result that the user has answered that the third disclosure item has a second preset status, and not executing the processing of the inputting of the statement that has been input into the input form for the first disclosure item into the input form for the second disclosure item based on the determination result that the user has answered that the third disclosure item does not have the second preset status, and wherein the first disclosure item and the second disclosure item are displayed in separate graphical display areas and the plurality of display elements of the third disclosure item are located within a graphical display area of the first disclosure item.

19. The information storage medium according to claim 18, wherein the program further causes the computer to perform a function of:
displaying, when the user inputs the statement into one of the input forms of the plurality of disclosure items, one or more statements that have been input into the input forms of one or more other disclosure items associated with a disclosure item, on the screen;
receiving the statement selected by the user among from the displayed statements; and
inputting, into the input form, the statement selected by the user among from the displayed statements.

20. The information storage medium according to claim 18, wherein the program further causes the computer to perform a function of:
displaying, when the user inputs the statement into one of the input forms of the plurality of disclosure items, a plurality of statement candidates on the screen, wherein
the receiving the input of the statement includes receiving the statement selected by the user from the plurality of statement candidates, and
the displaying the plurality of statement candidates includes preferentially displaying a statement candidate that has been input into the input form of another disclosure item associated with a disclosure item to be input over other statement candidates.

21. The information storage medium according to claim 18, wherein the program causes the computer to perform a function of:
receiving input from the user regarding a treatment or an examination of an injury/disease; and
determining whether the treatment or the examination of the injury/disease that has been input into the input form of another disclosure item associated with a disclosure item to be input relates to the disclosure item to be input.

22. The information storage medium according to claim 18, wherein the program causes the computer to perform a function of:
receiving input from the user regarding a name of an injury/disease or an examination; and
determining whether the name of the injury/disease or the examination that has been input into the input form of another disclosure item associated with a disclosure item to be input is the name relating to the disclosure item to be input.

23. The information storage medium according to claim 18, wherein the program causes the computer to perform a function of:
receiving input from the user regarding a period of a treatment or an examination of an injury/disease; and
determining whether the period of the treatment or the examination of the injury/disease that has been input into the input form of another disclosure item associated with a disclosure item to be input is the period relating to the disclosure item to be input.

24. The information storage medium according to claim 18, wherein the program further causes the computer to perform a function of:
displaying, when the user inputs the statement into one of the input forms of the plurality of disclosure items, a plurality of statement candidates on the screen;

receiving the input of the statement from the user by receiving the statement selected by the user from the plurality of statement candidates; and preferentially displaying a statement candidate that has been input into the input form of another disclosure item associated with a disclosure item to be input over other statement candidates.

25. The information storage medium according to claim 18, wherein the program further causes the computer to perform a function of:

restricting input of statements into respective input forms by the user;

releasing, when a releasing operation associated with each of the plurality of disclosure items is performed, a restriction of the input into the input form of a disclosure item;

determining, when the user inputs the statement into the input form that is released from the restriction, whether the statement input by the user relates to another disclosure item; and assuming that the releasing operation of the another disclosure item is performed based on the determination result.

* * * * *